United States Patent
Chenevert et al.

(10) Patent No.: US 6,567,684 B1
(45) Date of Patent: May 20, 2003

(54) IMAGING SYSTEM, COMPUTER, PROGRAM PRODUCT AND METHOD FOR DETECTING CHANGES IN RATES OF WATER DIFFUSION IN A TISSUE USING MAGNETIC RESONANCE IMAGING (MRI)

(75) Inventors: Thomas L. Chenevert, Ann Arbor, MI (US); Alnawaz Rehemtulla, Plymouth, MI (US); Brian D. Ross, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 136 days.

(21) Appl. No.: 09/732,362

(22) Filed: Dec. 6, 2000

Related U.S. Application Data

(60) Provisional application No. 60/247,388, filed on Nov. 8, 2000.

(51) Int. Cl.⁷ .............................................. A61B 5/055
(52) U.S. Cl. ..................... 600/410; 600/419; 600/544; 600/545; 324/309
(58) Field of Search ................................ 600/410, 411, 600/427, 419, 544, 545; 324/307, 306, 309

(56) References Cited

U.S. PATENT DOCUMENTS 6,463,315 B1 * 10/2002 Klingberg et al. .......... 600/410

OTHER PUBLICATIONS

Greenberg, et al., "*Tumor Imaging and Response,*" BRAIN TUMORS, Oxford Univ. Press, (1999) Ch. 3, pp. 58–77.
Macdonald, et al., "*Response Criteria for Phase II Studies of Supratentorial Malignant Glioma,*" J. of Clinical Oncology, vol. 8, No. 7 (1990) pp. 1277–1280.
Burdette, et al., "*Calculation of Apparent Diffusion Coefficients(ADCs) in Brain Using Two–Point and Six–Point Methods,*" J. of Computer Assisted Tomography, vol. 22, No. 5, (1998) pp. 792–794.
Stegman, et al., "*Diffusion MRI detects early events in the response of a glioma model to the yeast cytosine deaminase gene therapy strategy,*" Gene Therapy, vol. 7 (2000) pp. 1005–1010.
Norris et al., "*Healthy and Infarcted Brain Tissues Studied at Short Diffusion Times: the Origins of Apparent Restriction and the Reduction in Apparent Diffusion Coefficient,*" NMR in Biomedicine, vol. 7, (1994) pp. 304–310.
Ross et al., "*Magnetic Resonance Imaging and Spectroscopy: Application to Experimental Neuro–Oncology,*" Quart. Magn. Res. in Biol. Med., vol. I (1994) pp. 89–106.
Ross et al., "*In Vivo Magnetic Resonance Imaging and Spectroscopy and Imaging and Spectroscopy: Application to Brain Tumors,*" Magnetic Resonance Spectroscopy and Imaging in Neurochemistry, vol. 8 of Advances in Neurochemistry, (1997) pp. 145–178.

* cited by examiner

*Primary Examiner*—Hieu T. Vo
(74) *Attorney, Agent, or Firm*—Fish & Richardson P.C.

(57) ABSTRACT

The invention provides a computer-implemented method for detecting changes in rates of water diffusion in a tissue. The invention also provides a computer program product for use in the detection of changes in rates of water diffusion in a tissue using magnetic resonance imaging (MRI) comprising a computer useable medium comprising a computer readable program code embodied therein, wherein the computer program product is capable of storing and analyzing data input from a MRI device. The invention also provides a computer system, comprising a processor and a computer program product of the invention. The invention also provides a tissue imaging system, comprising a magnetic resonance imaging (MRI) device capable of outputting data to a processor; a processor; and, a computer program product of the invention embodied within the processor.

27 Claims, 12 Drawing Sheets

3F

3E

IMAGING SYSTEM, COMPUTER, PROGRAM PRODUCT AND METHOD FOR DETECTING CHANGES IN RATES OF WATER DIFFUSION IN A TISSUE USING MAGNETIC RESONANCE IMAGING (MRI)

This application claims the benefit of Provisional application Ser. No. 60/247,388, filed Nov. 8, 2000.

STATEMENT AS TO RIGHTS TO INVENTIONS MADE UNDER FEDERALLY SPONSORED RESEARCH

This invention was made in part with Government support under National Institutes of Health grants R24CA83099 and P20CA86442. The Government may have certain rights in the invention.

TECHNICAL FIELD

This invention generally pertains to the fields of medicine and cancer therapeutics. In particular, this invention provides compositions and methods for detecting changes in rates of water diffusion in a tissue of an individual. Thus; the invention also provides a non-invasive means to evaluate the effectiveness of a therapy for a disorder of cell growth, such as cancer.

BACKGROUND

Primary brain tumors account for more than 26% of childhood and 2% of adult cancer deaths in the United States. Sadly, improvements in five-year survival rates for brain tumor patients have been rather modest over the past 20 years despite significant advances in stereotactic neurosurgery and focal conformal radiation therapy. Progress in adjuvant chemotherapy has also been disappointing, with few demonstrable gains made since the initial trials of alkylnitrosoureas (e.g., BCNU) in 1978. The failure of new chemotherapeutic regimens to improve patient survival may be because less than 50% of tumors will respond to a given protocol. Adjuvant chemotherapy may be made more successful if the responsiveness of a tumor to a given protocol could be assessed in a more timely fashion than currently available, thereby, allowing trials of multiple regimens.

Currently, weeks to months pass before an evaluation of the effectiveness of a therapy for a CNS tumors is made. This evaluation involves examining changes in the maximal cross sectional area of a CNS tumor or the product of the maximal perpendicular tumor diameter. This involves comparison of sequential MRI scans; see, e.g., Buckner (1995) J. Neurosurg. 82:430–435; Grossman (1988) Semin. Oncol. 15:441–454; Vinitski (1988) J. Magn. Reson. Imaging 8:814–819; Watling (1994) J. Clin. Oncol. 12:1886–1889; James (1999) J. Natl. Cancer Inst. 91:523–528. Gadolinium-enhanced T1-weighted images are often used. T2-weighting or other MR contrast strategies are also employed. Comparisons of tumor burden are usually made between pre-treatment scans and those obtained weeks to months following the conclusion of a therapeutic protocol; see, e.g., Therasse (2000) J. Natl. Cancer Inst. 92:205–216.

Methods of assessing treatment responses that are not dependent on relatively slow changes in tumor volume may be capable of providing earlier indications of therapeutic outcome. In pursuit of this goal, attempts have been made to correlate changes in brain tumor biochemistry with therapeutic response using MR spectroscopy (see, e.g., Kurhanewicz (2000) Neoplasia 2:166–189; Ross, et al., "In vivo magnetic resonance imaging and spectroscopy: Application to brain tumors. In Magnetic Resonance Spectroscopy and Imaging in Neurochemistry;" Bachelard H, ed. New York: Plenum Press, 1997, pp 145–178) and [$^{18}$F] fluorodeoxyglucose PET imaging (see, e.g., Brock (2000) Br. J. Cancer 82:608–615.

SUMMARY

The invention provides a computer-implemented method for detecting changes in rates of water diffusion in a tissue. The method can be practiced in vitro, ex vivo or in vivo, as, in an individual. The method comprises the following steps: (a) providing a magnetic resonance imaging (MRI) device capable of outputting data to a computer; (b) providing a computer capable of storing and analyzing data input from the MRI device comprising a computer program product embodied therein; (c) projecting a sequence of magnetic field gradient pulses and radiofrequency pulses to the tissue of interest by the MRI device and collecting a first set of MRI signals from the tissue and outputting this data to the computer, wherein the MRI device collects MRI signals from the tissue of interest at multiple diffusion sensitivities and diffusion directions; (d) analyzing the first set of diffusion-sensitive MRI signal readings by the computer program product to calculate an apparent diffusion coefficient (ADC) value for each diffusion direction, wherein an ADC value corresponds to a spatial origin of the signals used to determine the ADC value, and to generate a first spatial map of ADC values; (e) projecting at least a second sequence of magnetic field gradient pulses and radiofrequency pulses and analyzing at least a second set of diffusion-sensitive MRI readings in the same tissue of interest as in steps (c) and (d) to generate at least a second subsequent spatial map of ADC values; and (f) compare the first and subsequent spatial maps of ADC values to generate a spatial map that reflects the changes in ADC values over the time the several readings were taken by the MRI, wherein the changes in ADC values reflect the changes in spin diffusion properties which reflect changes in rates of water diffusion in the tissue.

In one embodiment of the computer-implemented method of the invention, the computer program product uses the spatial map that reflects the changes in ADC values over the time the several readings were taken by the MRI to generate a histogram (see Example 1, below, for examples of histograms).

In one embodiment, an increase in the rate of water diffusion as shown by the spatial map that reflects the changes in ADC values over the time taken by the MRI indicates cell damage or tissue microvasculature damage. A rate of water diffusion higher or lower than considered normal for the tissue of interest can indicate cell damage or tissue microvasculature damage.

In alternative embodiments, tissue or body section of interest imaged by the methods of the invention is brain or spinal cord tissue, an internal organ, a skeletal and a muscle tissue. The tissue or body section of interest imaged by the methods of the invention can be normal, injured or inflamed tissue or diseased tissue; or, tissues in the process of aided or unaided treatment or therapy. For example, the diseased tissue can be a cancer, such as a solid tumor. The tissue can have been exposed to a drug, a biological agent, hyperthermia, hypothermia, a radiation or a combination thereof. The tissue can have been exposed to an antivascular therapy. In one embodiment, the radiation is a radiotherapy or a photodynamic therapy or a combination thereof.

In alternative embodiments, the computer-implemented method of the invention can determine the effectiveness of an organ or a tissue transplant or a therapy for a condition or a disease or an injury. For example, the therapy can be for a cancer, such as a sold tumor. An increase in diffusion indicates tumor cell damage or tumor microvasculature damage, thereby indicating the effectiveness of the therapy. In another embodiment, a change in diffusion indicates tissue repair. For example, the therapy can be for an injured or inflamed tissue and a charge in diffusion indicates tissue repair or decreased inflammation, thereby indicating the effectiveness of the therapy.

In one embodiment, the ADC values from a defined spatial subsection of the tissue taken over time is used to generate a statistical data reduction of data in that spatial subsection. The statistical data reduction can comprise a mean, a standard deviation, a pixel count or a volume of tissue or a combination thereof.

In one embodiment, the computer-implemented method generates a histogram from the statistical data reduction. The histogram can reflect changes in statistical data reduction sets over time.

In one embodiment, a first set of diffusion-sensitive MRI signal readings is generated before initiation of a therapy. Subsequent sets of diffusion-sensitive MRI signal readings can be generated after initiation of a therapy. A subsequent set of diffusion-sensitive MRI signal readings can be generated at a time appropriate for a therapeutic change to be apparent in tissue. If therapeutic changes in tissue as quantified by the methods of the invention via diffusion MRI are insufficient, a change in therapy may be indicated, e.g., in the treatment of a tumor, a change from radiotherapy to chemotherapy, or, vise versa.

The invention also provides a computer program product for use in the detection of changes in rates of water diffusion in a tissue using magnetic resonance imaging (MRI) comprising a computer useable medium comprising a computer readable program code embodied therein, wherein the computer program product is capable of storing and analyzing data input from a MIM device by a process comprising the following steps: (a) providing a magnetic resonance imaging (MRI) device capable of outputting data to a computer; (b) providing a computer capable of storing and analyzing data input from the MRI device comprising a computer program product embodied therein; (c) projecting a sequence of magnetic field gradient pulses and radio-frequency pulses to the tissue of interest by the MRI device and collecting a first set of MRI signals from the tissue and outputting this data to the computer, wherein the MRI device collects MRI signals from the tissue of interest at multiple diffusion sensitivities and diffusion directions; (d) analyzing the first set of diffusion-sensitive MRI signal readings by the computer program product to calculate an apparent diffusion coefficient (ADC) value for each diffusion direction, wherein an ADC value corresponds to a spatial origin of the signals used to determine the ADC value, and to generate a first spatial map of ADC values; (e) projecting at least a second sequence of magnetic field gradient pulses and radio-frequency pulses and analyzing at least a second set of diffusion-sensitive MRI readings in the same tissue of interest as in steps (c) and (d) to generate at least a second subsequent spatial map of ADC values; and, (f) compare the first and subsequent spatial maps of ADC values to generate a spatial map that reflects the changes in ADC values over the time the several readings were taken by the MRI, wherein the changes in ADC values reflect the changes in spin diffusion properties which reflect changes in rates of water diffusion in the tissue.

The invention also provides a computer system, comprising a processor and a computer program product of the invention. The invention also provides a tissue imaging system, comprising: (a) a magnetic resonance imaging (MRI) device capable of outputting data to a processor; (b) a processor; and, (c) a computer program product of the invention embodied within the processor.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

Like reference symbols in the various drawings indicate like elements.

DETAILED DESCRIPTION

Figure 1A:
FIG. 1A shows quantitative ADC maps of a representative rat brain obtained pre-treatment (day 0) and 8, 20, and 28 days after administration of an anti-cancer agent.

The invention provides a computer-implemented method for detecting changes in rates of water diffusion in a tissue. By detecting changes in water diffusion in a tissue over time, the invention provides methods for detecting changes in the states of those cells and tissues. Thus, the methods of the invention also provide methods for monitoring changes in the physiology or the health of a collection of cells or a tissue. These methods are particularly useful for monitoring the effectiveness of a treatment or a healing process. For example, in cancer therapy, the objective of the treatment is to cause the death of tumor cells. Any tissue incurring a significant amount of cell death will have a decrease in tissue cellularity and a corresponding increase in the rate of water diffusion; conversely, a decrease in cell death or inflammation over time will have a decrease in water diffusion. Thus, computer-implemented methods of the invention are particularly effective non-invasive, non-toxic means to evaluate the effectiveness of a cancer treatment. "Diffusion magnetic resonance imaging" can reveal rapid changes in tumor cellularity by imaging changes in tumor water diffusion values after a successful therapeutic intervention.

While the invention is not limited by any particular mechanism of action, Monte Carlo simulations suggest that changes in tissue water diffusion following tissue damage (e.g., successful anti-tumor therapy) are predominantly attributable to alterations in the volume and tortuosity of the extracellular space; see, e.g., Szafer (1995) Magn. Reson. Med. 33:697–712; Sykova (1994) J. Cereb. Blood Flow Metab. 14:301–311; Norris (1994) NMR Biomed. 7:304–310. These properties of the extracellular space are primarily a function of cell density. Thus, diffusion-weighted MRI (DWI) is measuring tumor water diffusion correlated with the volume and tortuosity of the extracellular space and tumor cellularity; see, e.g., Sugahara (1999) J. Magn. Reson. Imaging 9:53–60; Lyng (2000) Magn. Reson. Med. 43:828–836. Diffusion-weighted MRI (DWI) has also proven to be a sensitive technique for identifying regions of ischemic tissue damage in animal models of stroke and in human patients; see, e.g., Moseley (1990) Magn. Reson. Med. 14:3307346; Warach (1990) Ann. Neurol. 37:231–241; Sorensen (1996) Radiology 199:391–401. Ross (1994) Quart. Magn. Reson. Biol. Med. 1:89–106 reported elevation of mean tumor apparent diffusion coefficient (ADC) following. 1,3 bis (2-chloroethyl)-1-nitrosourea (BCNU) treatment of the orthotopic 9L glioma model. Chinnaiyan (2000) Proc. Natl. Acad. Sci. USA 97:1754–1759, found that treatment of orthotopic MCF7 breast tumors in nude mice with TNF-related apoptosis inducing ligand (TRAIL) produced an increase in tumor diffusion that preceded tumor regression. Stegman (2000) Gene Therapy 7:1005–1010, found that treatment of orthotopic 9L gliomas with gene therapy similarly produced an increase in tumor diffusion that preceded tumor regression. Hakumaki (1998) Cancer Res. 58:3791–3799, and Poptani (1998) Cancer Gene Ther. 5:101–109, demonstrated therapy-induced diffusion increases in brain tumor models following gene therapy. Galons (1999) Neoplasia 1:113–137, demonstrated diffusion increases in breast tumor models treated with Paclitaxel. Zhao (1996) Br. J. Cancer 73:61–64, demonstrated diffusion increases in murine RIF-1 tumors treated with cyclophosphamide.

The MRI device collects MRI signals from the tissue of interest via a sequence of magnetic field gradient pulses and radiofrequency pulses. The device collects data at multiple diffusion sensitivities and diffusion directions. The diffusion properties (diffusion sensitivities and diffusion directions) of the nuclear spins that comprise the MRI signal have a measurable affect on the strength of the MRI signal. Thus, the diffusion effect is more specifically determined.

A diffusion MRI reading comprises at least two signals and at least two spin readings comprising a first magnetic resonance signal and reading followed, after a defined pause in time, by a second gradient pulsed magnetic resonance signal and reading. The reading data is outputted to the computer. A comparison of the first and subsequent sets of apparent diffusion coefficient (ADC) maps is compared to generate spatial maps. These spatial maps reflect the change in spin diffusion properties over time from all sections of tissue imaged by the MRI.

Studies demonstrating the effectiveness of therapy for individual brain cancer patients using the methods of the invention are described in Example 1, below. The effectiveness of therapy was evaluated by measuring changes in tumor water diffusion, and thus tumor volume, using the methods of the invention. The study demonstrated the dose-dependent sensitivity of diffusion MRI for detection of early therapeutic-induced changes in tumor water diffusion. A rodent brain tumor model was also used. Clinical data demonstrated that early ADC measures of human brain tumors are indeed predictive of treatment response. The studies described in Example 1 indicate that diffusion MRI data as collated by the methods of the invention is a very sensitive technique able to detect relatively low levels of tumor cell kill. These data support the hypothesis that the magnitude change in tumor water diffusion assessed using MRI is related to the numbers of cells killed and hence therapeutic efficacy. Moreover, the maximal diffusion change preceded tumor shrinkage, demonstrating that diffusion parameters as generated by the methods of the invention are useful as early predictors of therapeutic response in tumors, particularly brain tumors.

In the studies described in Example 1, neuroimaging studies were obtained 6 to 8 weeks after conclusion of an anti-cancer treatment cycle to provide an early treatment response profile. Thus, the methods of the invention provide a capability that will improve the survival of brain tumor patients by providing more time for secondary therapeutic interventions, if necessary. These studies examined, inter alia, the sensitivity of diffusion MRI measurements using the orthotopic 9L glioma animal model. Also provided are clinical examples of the methods of the invention on human patients.

As discussed in Example 1, using the methods of the invention, water diffusion changes in orthotopic 9L gliomas were detected following chloroethylating nitrosourea (the alkylnitrosoureas lomustine, fotemustine, cystemustine, or, 1,3 bis (2-chloroethyl)-1-nitrosourea, i.e., "BCNU") doses eliciting as little as 0.2 log cell kill. Mean tumor apparent diffusion coefficients were found to be correlated with and highly sensitive to changes in tumor cellularity. The feasibility of the methods of the invention (incorporating serial diffusion MRI) in the clinical management of primary brain tumor patients was also demonstrated. Increased diffusion values were detected in human brain tumors shortly following treatment initiation. The magnitude of the diffusion changes corresponded with clinical outcome. These results demonstrate that the methods of the invention provide an early surrogate marker for quantifying treatment response in patients with solid tumors.

Definitions

Unless defined otherwise, all technical and scientific terms used herein have the meaning commonly understood by a person skilled in the art to which this invention belongs. As used herein, the following terms have the meanings ascribed to them unless specified otherwise.

As used herein, the term magnetic resonance imaging (MRI) device incorporates all devices capable of magnetic resonance imaging or equivalents. The methods of the invention can be practiced using any such device, or variation of an MRI device or equivalent, or in conjunction with any known MRI methodology. In magnetic resonance methods and apparatus a static magnetic field is applied to a tissue or a body under investigation in order to define an equilibrium axis of magnetic alignment in a region of interest. A radio frequency field is then applied to that region in a direction orthogonal to the static magnetic field direction in order to excite magnetic resonance in the region. The resulting radio frequency signals are detected and processed. The exciting radio frequency field is applied. The resulting signals are detected by radio-frequency coils placed adjacent the tissue or area of the body of interest. See, e.g., U.S. Pat. Nos. 6,144,202; 6,128,522; 6,127,825; 6,121,775; 6,119,032; 6,111,410; 602,891; 5,555,251; 5,455,512; 5,450,010; 5,378,987; 5,214,382; 5,031,624; 5,207,222; 4,985,678; 4,906,931; 4,558,279. MRI and supporting devices are manufactured by, e.g., Bruker Medical GMBH; Caprius; Esaote Biomedica; Fonar; GE Medical Systems (GEMS); Hitachi Medical Systems America; Intermagnetics General Corporation; Lunar Corp.; MagneVu; Marconi Medicals; Philips Medical Systems; Shimadzu; Siemens; Toshiba America Medical Systems; including imaging systems, by, e.g., Silicon Graphics.

As used herein, the terms "computer" and "processor" are used in their broadest general contexts and incorporate all such devices. The methods of the invention can be practiced using any computer/processor and in conjunction with any known software or methodology. For example, a computer/processor can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage.

The methods of the invention incorporate MRI diffusion-weighted imaging (DWI). Briefly, this approach is based on the measurement of Brownian motion of molecules and the fact that nuclear magnetic resonance is capable of quantifying diffusional movement of molecules. Diffusion imaging is a method that combines this diffusion measurement with MRI. This technique can characterize water diffusion properties at each picture element (pixel) of an image. For example, diffusion imaging can detect water diffusion in highly ordered organs, such as brains. In these organs, water does not diffuse equally in all directions, a property called anisotropic diffusion. For example, brain water diffuses preferentially along axonal fiber directions; see, e.g., Basser (2000) Magn. Reson. Med. 44:625–632.

The methods of the invention can also incorporate other MRI protocols and analysis methodologies, e.g., the Fluid-Attenuated Inversion Recovery (FLAIR) pulse sequence protocol. See, e.g., U.S. Pat. Nos. 6,023,634; 5,751,145; Husstedt (2000) Eur. Radiol. 10:745–752; Essig (1998) J. Magn. Reson. Imaging 8:789–798; Tsuchiya (1996) AJNR Am. J. Neuroradiol. 17:1081–1086.

The methods of the invention can be practiced in conjunction with any situation where detection of changes in rates of water diffusion in a tissue would be useful, such as in a medical therapy, including, e.g., treatments of an injury or a pathology, such as a tumor, particularly, a pathology or tumor within a bony structure, such as a brain tumor or other intracranial lesion, e.g. a granuloma, a cyst, hemorrhage (intracerebral, extradural, or subdural), aneurysm, abscess, and the like.

Common primary childhood tumors are cerebellar astrocytomas and medulloblastomas, ependymomas, gliomas of the brain stem and optic nerve, germinomas, and congenital tumors. The most common metastatic tumors in children are neuroblastoma (usually epidural) and leukemia (meningeal). In adults, primary tumors include meningiomas, schwannomas, primary lymphomas, and gliomas of the cerebral hemispheres (particularly the malignant glioblastoma multiforme and anaplastic astrocytoma and the more benign astrocytoma and oligodendroglioma). Metastatic tumors in adults arise most commonly from bronchogenic carcinoma, adenocarcinoma of the breast, and malignant melanoma.

A number of embodiments of the invention have been described. Nevertheless, it will be understood that various modifications may be made without departing from the spirit and scope of the invention. Accordingly, other embodiments are within the scope of the following claims.

EXAMPLES

The following example is offered to illustrate, but not to limit the claimed invention.

Example 1

Early Monitoring of Brain Tumor Therapy in Animals and Humans

The following example demonstrates that the methods of the invention can be used to evaluate the efficacy of a treatment against a brain cancer very early after the beginning of the anti-cancer therapy.

This study demonstrated the effectiveness of therapy for individual brain cancer patients using the methods of the invention. The effectiveness of therapy was evaluated by measuring changes in tumor water diffusion, and thus tumor volume, using the methods of the invention. The study demonstrated the dose-dependent sensitivity of diffusion MRI for detection of early therapeutic-induced changes in tumor water diffusion. Clinical data demonstrated that early ADC measures of human brain tumors are indeed predictive of treatment response. A rodent brain tumor model was also used to demonstrate the effectiveness of the invention.

Animal Model

Rat 9L glioma cells were obtained from the Brain Tumor Research Center at the University of California at San Francisco and grown as monolayers in minimal essential medium supplemented with 10% fetal calf serum, 100 IU/ml penicillin and 100 mg/ml streptomycin, and 2 mM L-glutamine at 37° C. in a 95/5% air/$CO_2$ atmosphere. Intracerebral 9L tumors were induced in male Fischer 344 rats weighing between 125 and 135 gram (g) as described by Ross (1998) Proc. Natl. Acad. Sci. USA 95:7012–7017. Briefly, 9L cells ($10^5$) were implanted in the right forebrain at a depth of 3 mm through a 1 mm burr hole. The surgical field was cleaned with 70% ethanol and the burr hole was filled with bone wax to prevent extracerebral extension of the tumor. BCNU was dissolved in absolute ethanol and diluted in saline at the time of treatment and administered by a single intraperitoneal (i.p.) injection at a dose of 0.5 (n=5), 1.0 (n=5) and 2.0 (n=6) $LD_{10}$ corresponding to 6.65, 13.3, and 26.6 mg/kg, respectively. Control 9L animals (n=6) received injections of vehicle (10% ethanol in saline) only.

Animal Diffusion Magnetic Resonance Imaging

Imaging was performed every other day beginning 10 days after tumor cell implantation on a Varian Unity Inova system equipped with at 7.0 tesla, 18.3 cm horizontal bore magnet (Oxford Instruments Inc.) and a quadrature rat head coil (USA Instruments, Inc.). For MRI examination, rats were anesthetized with an isofluorane/air mixture and maintained at 37° C. inside the magnet using a heated, thermostated circulating water bath. A single-slice sagittal gradient-echo sequence was used to confirm proper animal positioning and to prescribe subsequent acquisitions. For time-efficient acquisition, an isotropic, diffusion-weighted sequence (as described by Wong (1995) Magn. Reson. Med 34:139–143) was employed with 2 interleaved b-factors ($\Box$b=1148 s/mm$^2$) and the following acquisition parameters: TR/TE=3500/60 ms, 128×128 matrix, and a 3 cm FOV (Burdette (1998) J. Comput. Assist. Tomogr. 22:792–794, has shown that there are no significant differences in apparent diffusion coefficient (ADC) values measured by faster two-point diffusion techniques versus six b-factor methods). Thirteen 1-mm thick slices separated by a 0.2-mm gap were used to cover the whole rat brain. The z-gradient first moment was zeroed to reduce the dominant source of motion artifact. To further reduce motion artifact, a 32-point navigator echo was prepended to each phase-encode echo, as described by Ordidge (1986) J. Magn. Reson. 66:283, and Anderson (1994) Magn. Reson. Med. 32:379–387. The phase deviation of each navigator echo relative to their mean was subtracted from the respective image echoes prior to the phase-encode Fourier transform. The low b-factor images were essentially T$_2$-weighted to allow tumor volume measurements, as described by Ross (1998) supra.

Images were acquired prior to treatment and at two-day intervals thereafter. Isotropic ADC maps were calculated for each image set and ADC pixel value histograms were generated from tumor ROI's combined across slices. For the dose-response studies, localized diffusion measurements were taken from a column of tumor tissue, as described by Chenevert (1997) Clin. Cancer Res. 3:1457–1466. Briefly, T2-weighted images were used to prescribe a 2×2 mm column through the most homogenous, non-cystic region of the tumor and contralateral brain from which diffusion measurements were made. Motion artifacts were minimized by employing a frequency encode gradient along the column axis for spatial encoding and magnitude processing of Fourier transformed echoes. Diffusion gradients at 42 b-factors ranging from 87–1669 s/mm$^2$ were independently applied on the x, y, and z axes. Apparent diffusion coefficient (ADC) values were calculated as the quantity ADC=(ADC$_x$+ADC$_y$+ADC$_z$)/3, which represents a scalar invariant of the 3×3 diffusion tensor normally used to fully characterize diffusion in an anisotropic system.

Histological Analysis

In a separate study, rats (n=24) were implanted intracerebrally with 9L cells. At 12 days post-cell implantation, BCNU was administered at a dose of 26.6 mg/kg i.p. (n=18) or control vehicle (n=6). Rats were sacrificed in groups of three for histological analysis at days 0 (vehicle-only), 2, 4, 8, 16 and 20 (vehicle-only and BCNU-treated) post-treatment. Brain specimens were removed, fixed in 10% buffered formaldehyde, sectioned (6 $\mu$m) and stained with H & E. Randomly selected 400× fields were captured and digitized with a Pixera VCS 110™ camera interfaced with a Macintosh PowerPC™ computer. Cellularity measurements were made with Scios Image™ by segmenting the images based on signal intensity. The intensity and minimum particle size thresholds were set by one individual (LDS) who was blinded to the treatment which the animal received and the post-therapy time at which the section was obtained. Comparisons of tumor cellularity with ADC values were made using simple linear regression analysis.

Human Subjects

Preliminary evaluation of the clinical potential of diffusion MRI was performed in two patients with primary CNS tumors. Patients recruited for this study were required to have a malignant brain tumor histologically confirmed as: glioblastoma multiforme, anaplastic astrocytoma, anaplastic oligodendroglioma, or primitive neuroectodermal tumor (PNET), either at initial diagnosis or at the time of tumor relapse, and were to undergo radiation, chemo-radiation, or chemotherapy. Of the initial three subjects enrolled in the study, one subject suffered a stroke during their treatment and was excluded from further study as it is known diffusion MRI is sensitive to stroke-induced changes. The remaining two subjects are presented here.

Patient 1

A 13 year old female underwent a craniotomy for a small partial resection of a supratentorial thalamic PNET. Two baseline MRIs were performed before the start of radiotherapy that was given in standard daily fractions of 1.8 Gy, 5 days per week to a total dose of 55.8Gy. Concurrent carboplatin was given daily as a radiosensitizer, one hour before each radiation fraction. Cyclophosphamide was then given as adjuvant chemotherapy in 6 cycles at a dose of 2 grams/cycle, over a 7-month period spanning 3 to 10 months from the start of therapy. One cycle of salvage chemotherapy with cisplatin, CCNU, and vincristine was given at tumor progression, 11 months after initial treatment. The patient succumbed to her disease 14 months from diagnosis.

Patient 2

A 37 year old male with an anaplastic oligodendroglioma of the right temporofrontal region that was partially resected 1 month prior to initiation of treatment with 6 cycles of procarbazine, vincristine, and CCNU chemotherapy. Each cycle consisted of CCNU 130 mg/m$^2$, day 1, procarabazine 75 mg/m$^2$ days 8–21, and vincristine 1.5 mg/m$^2$ day 8 and 29. Following 6 cycles of this therapy the patient progressed on MRI scan and was treated with conformal radiation therapy. One year following diagnosis the patient is doing well clinically without neurologic deficit and is followed with serial scans at four-month intervals.

Standard MR sequences including T1-weighted with contrast enhancement, T2-weighted and FLAIR were acquired along with diffusion-weighted MR images before, during and following treatment to quantitate changes in tumor diffusion values for correlation with clinical response. Clinical outcomes were classified as complete response (CR), partial response (PR), stable disease (SD), and progressive disease (PD) which are defined as: CR: complete resolution of tumor contrast enhancement off all steroids; PR:>50% decrease in tumor volume on stable or decreased dose of steroids; SD:<50% decrease or <25% increase in tumor volume on stable or decreased dose of steroids; PD:>25% increase in tumor volume on stable or increased dose of steroids. Written informed consent was obtained from all subjects, and all images and medical records were obtained according to protocols approved by the University of Michigan Medical School Institutional Review Board.

Human Diffusion Magnetic Resonance Imaging. Water diffusion-sensitive images of the brain were acquired on a 1.5T Human MRI System™ (General Electric Medical Systems, Milwaukee, Wis.); capable of single-shot echo-planar imaging (EPI), as described by Turner (1990) Radiology 177:407–414. The diffusion spin-echo EPI sequence (TR/TE=10,000/100 msec) was set to acquire 14, 6 mm-thick, contiguous axial-oblique sections through the brain at a given diffusion sensitivities (i.e. "b factors") along all three orthogonal directions. A set of diffusion-weighted images at high diffusion sensitivity (b2=1000 sec/mm$^2$) and low sensitivity (b1=100 sec/mm$^2$) plus b=0 (i.e. T2-weighted) were collected in 80 seconds.

Diffusion-weighted images were reduced to ADC diffusion maps according to:

$$ADC_i = \frac{1}{(b2-b1)}\log_e\left[\frac{S_{b1}}{S_{b2}}\right]; ADC_o = \frac{[ADC_x + ADC_y + ADC_z]}{3};$$

where Sb1 and Sb2 are signal intensities at low and high diffusion weighting respectively, as acquired independently along each orthogonal axis. The quantity, ADCo, is a scalar-invariant of the diffusion tensor. Thus, it avoids complexities introduced by anisotropy in brain tissue, as described by Moseley (1990) Radiology 176:439–445; Chenevert (1990) Radiology 177:401–405; Basser (1994) Biophys. J. 66:259–267. The quantity, ADCo was generated using AVS 5™ (Advanced VisualSystems Inc, Waltham Mass.) and MatLab 5™ (MathWorks Inc, Natlick, Mass.) software routines. Tumor water diffusion was summarized by histograms of tumor ADC pixel values across all slices. Neuro-oncologists guided ROI definition along tumor boundaries using all available images.

Statistics

The individual pixel values comprising ADC histograms are spatially correlated. In order to calculate a standard error for the mean ADC value of each histogram, we sampled the set of pixels to obtain an approximately independent set. Software was written to randomly sample of 1% of pixels in each histogram. The standard deviation of the means from 25 such random sub-samples was used as a conservative estimate of the standard error of the original histogram. Differences between baseline and follow-up histograms were explored using the Bonferroni corrected t-test. For the rodent BCNU dose-response study, the one-way ANOVA test was used to search for statistical differences between localized ADC measurements at progressive time points following treatment and the pre-treatment ADC value. Pearson product moment correlation analysis and simple linear regression were used to examine the relationship between mean tumor ADC and cell density measurements. A significance level of $P=0.05$ was used throughout.

RESULTS

Rodent Studies

The effectiveness of the methods of the invention were demonstrated using art-recognized animal models. A rodent brain tumor model was used (see protocol, above). Time-course ADC maps from a representative animal treated with a bolus $2\times LD_{10}$ dose of BCNU are shown in FIG. 1A. Quantitative ADC maps of a representative rat brain obtained pre-treatment (day 0) and 8, 20, and 28 days after administration of a bolus $2\times LD_{10}$ BCNU dose. Thresholds set in the ADC calculation routine assign low signal-to-noise pixels as black for exclusion from subsequent analysis.

Figures 1B, 1C, 1D:
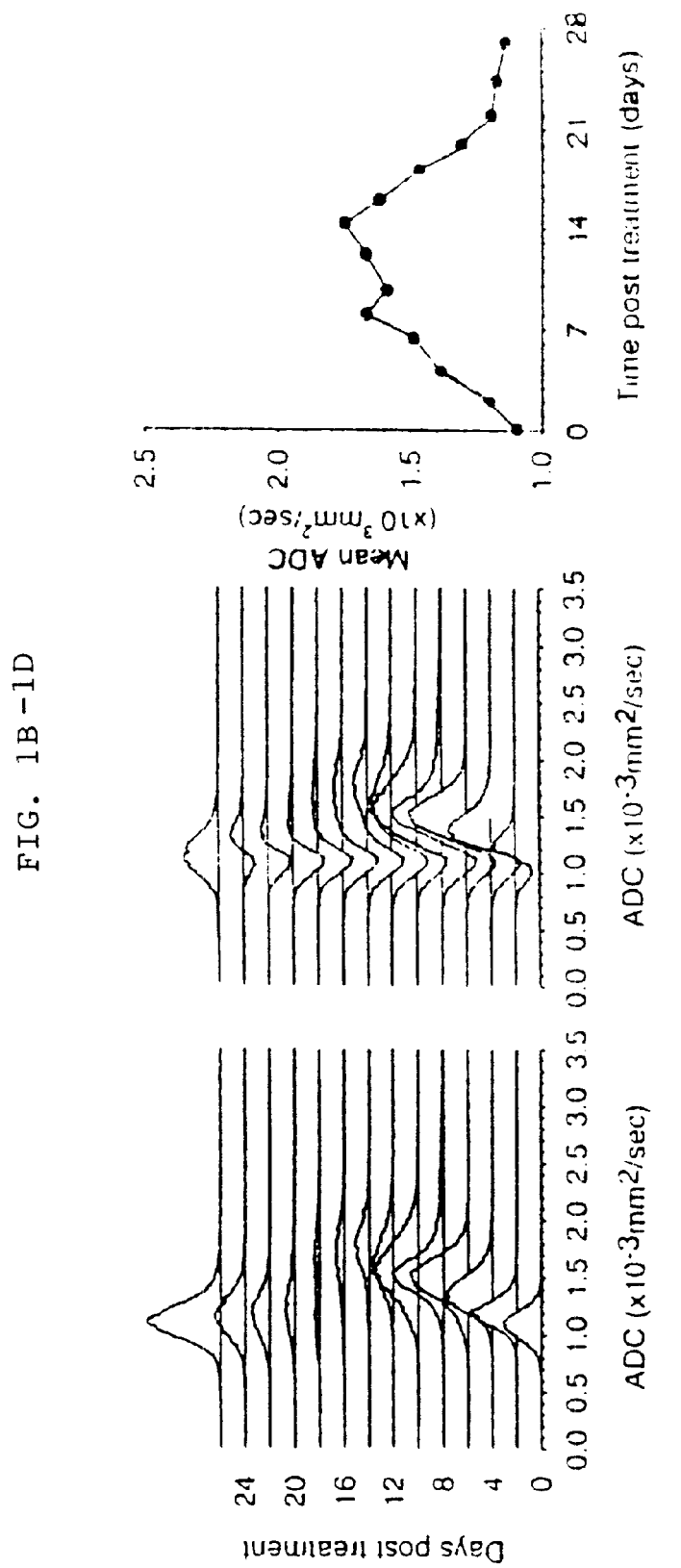
FIG. 1B shows serial ADC histograms of these data.
FIG. 1C shows difference-from-baseline histograms of these data.
FIG. 1D shows a plot of time-course of the mean tumor ADC value.

Although the tumor continued to grow over the first 8 days following BCNU-administration, it is apparent that the diffusibility of water in the tumor has increased relatively uniformly. The tumor continues to appear hyper-intense on ADC maps while it regresses. To quantitate changes in tumor water diffusion, regions of interest were defined for the tumor volume and histograms of tumor pixel ADC values were generated. The serial ADC histograms shown for this representative tumor (FIG. 1B), demonstrate a right-shift in tumor water diffusion beginning by the second post-therapy day, despite continued tumor growth reflected by an increase in the area under the histogram. Water diffusibility appeared to peak around day 8, after which the tumor began to regress. Eventually the small surviving fraction of tumor cells repopulate the tumor volume, resulting in a recurrent tumor with a water environment resembling that of the primary tumor prior to BCNU-treatment. This trend is demonstrated in the plot of mean tumor ADC versus time (FIG. 1B). Diffusion histograms permit segmentation of tumor pixels that exhibit "high-diffusion" properties, postulated to be sub-elements of the tumor responding to treatment. For example, the shaded region in the histograms (FIG. 1B) illustrate the volume of tumor pixels above an arbitrarily-selected ADC threshold of $1.5\times 10^{-3}$ mm$^2$/sec, which may indicate the fractional volume of tumor that exhibits a strong therapeutic response.

Difference-from-baseline histograms (FIG. 1C), calculated by subtracting the pre-treatment histogram from the histograms at each subsequent timepoint, emphasize the relative shifts in the tumor water diffusion subenvironments (difference histograms are calculated by subtracting the first (pre-treatment) histogram from each of the other time points to demonstrate the relative shift of pixels between different water environments). FIG. 1D is a plot of time-course of the mean tumor ADC value.

Figures 1E, 1F, 1G:
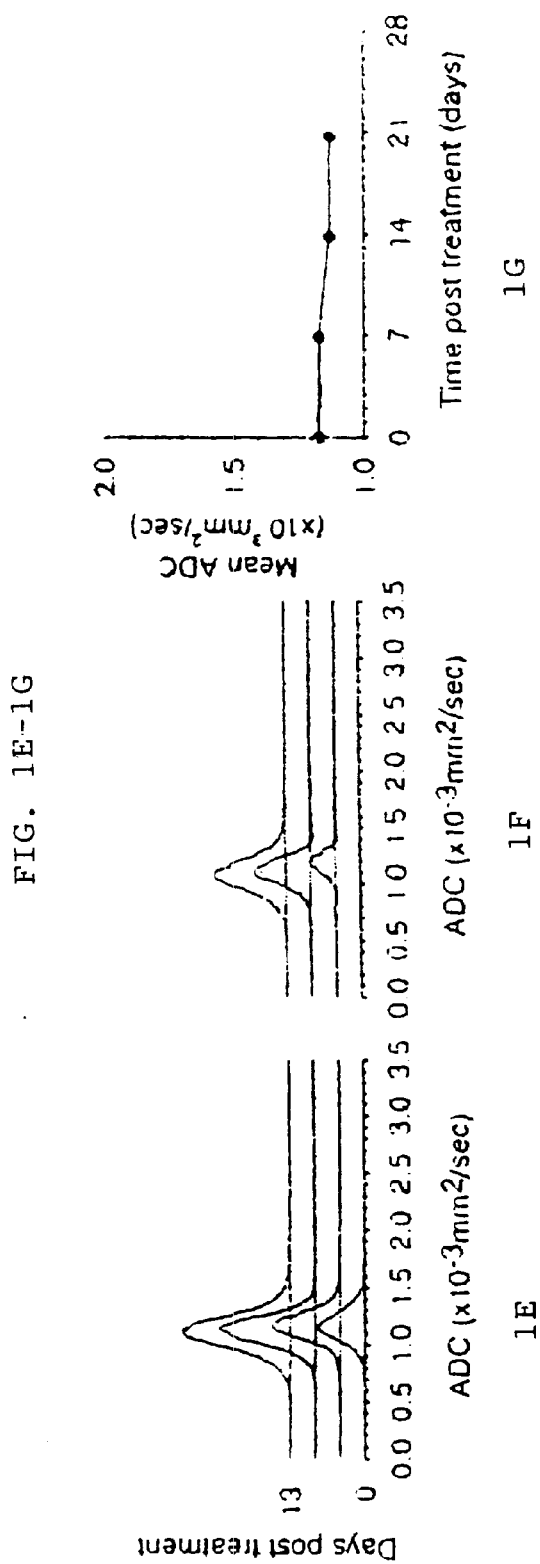
FIGS. 1E, 1F, and 1G show diffusion histograms and mean ADC results obtained from a representative, vehicle-only treated 9L tumor; as described in detail in Example 1, below.

Diffusion histograms and mean ADC results obtained from a representative, vehicle-only treated 9L tumor are shown in FIGS. 1E to 1G. FIG. 1E is an ADC histogram. FIG. 1F is a difference histogram. FIG. 1G plots mean tumor ADC time-course from a representative. control animal sham-treated with vehicle alone. The ADC value of normal contralateral brain in the BCNU-treated and control animals were constant ($0.90\pm0.07$, Mean$\pm$SD, n=14 time points and $0.87\pm0.01$, Mean$\pm$SD, n=4 time points, respectively) over the course of the experiment. Note that diffusion values are stable throughout the growth of the intra-parenchymal brain tumor.

Rat Dose-Response Studies

Figure 2:
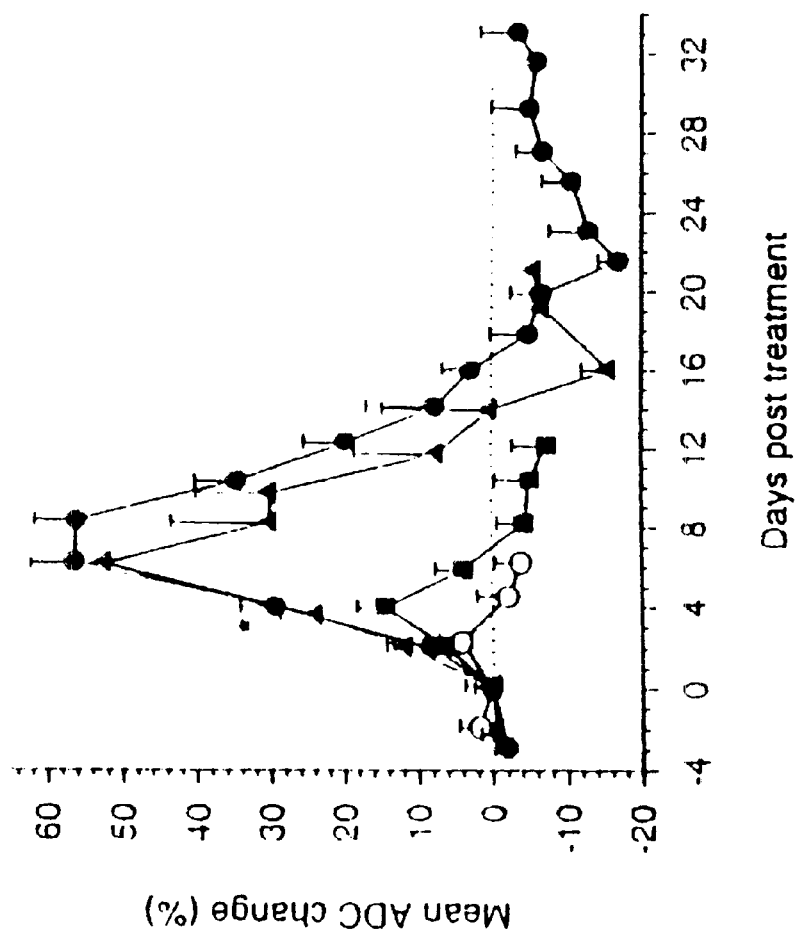
FIG. 2 is a plot of changes in mean tumor ADC values relative to the mean baseline tumor ADC in experiments assessing the dose-dependence and sensitivity of treatment-induced diffusion changes in a rat tumor model, as described in detail in Example 1, below.

To assess the dose-dependence and sensitivity of treatment-induced diffusion changes in the rat model, experiments were performed on intra-cranial 9L gliomas following administration of three different doses of BCNU. FIG. 2 shows dose dependence of BCNU-induced changes in tumor water diffusion. FIG. 2 is a plot of changes in mean tumor ADC values relative to the mean baseline tumor ADC measured at the beginning of the experiment. There is a clear dose-dependence in both the magnitude and duration of tumor diffusion changes. Statistically significant differences between each treatment group and the control group were first apparent at day 4 post-treatment. At the 2× and $1\times LD_{10}$ doses of BCNU, the absolute increase in the diffusion values were similar but the duration of the increase was slightly longer for the $2\times LD_{10}$ dose.

In FIG. 2, BCNU was given as a single i.p. bolus of 6.6 (■, n=5), 13.3(▲, n=6), and 26.6(●, n=6) mg/kg body weight, corresponding to 0.5×, 1×, and 2× the $LD_{10}$ dose, respectively. Control animals (○, n=5) were sham-treated with vehicle alone. Tumor ADC values were obtained using the voxel-method at 2T, as described by Chenevert (1997) Clin. Cancer Res. 3:1457–1466; and are given as means±SEM normalized to standard diffusion mapping ADC values. Differences between the treatment and control groups became statistically significant ($P<0.019$) at post treatment day 4 as determined by one-way ANOVA (*).

Cellularity and Diffusion Studies in the Rat Model

Figures 3A, 3B:
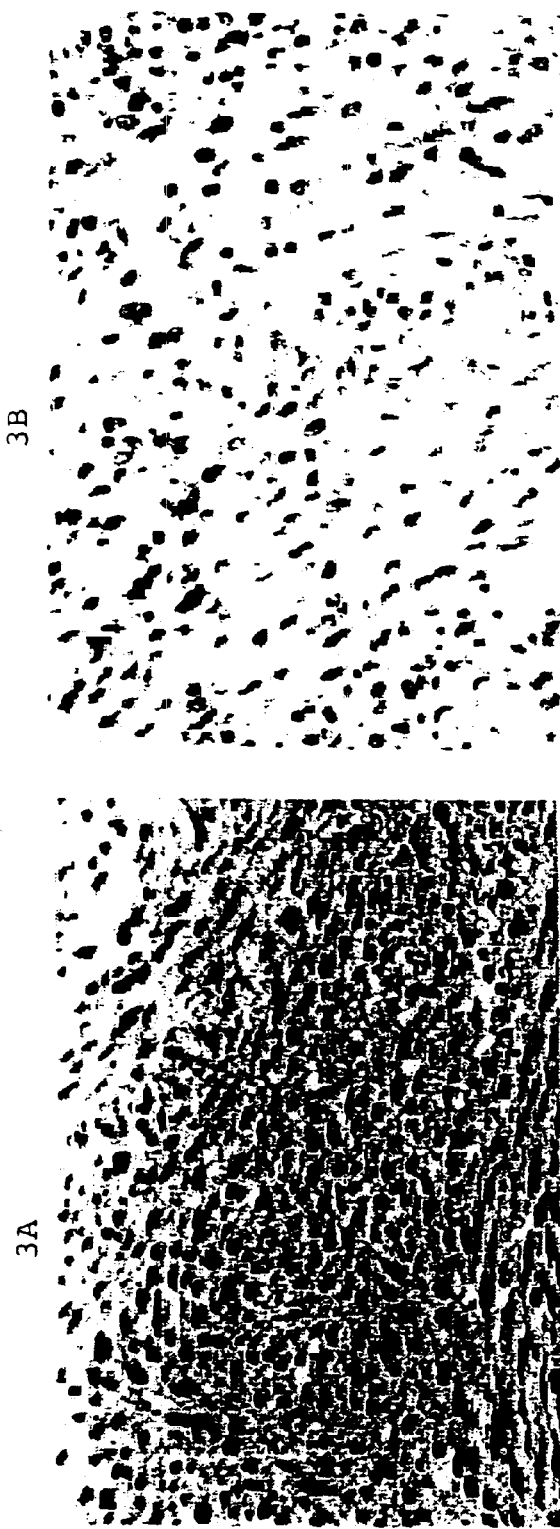
FIGS. 3A to 3F show histological sections of tumors in the rat experimental model at selected intervals following anti-cancer treatment.
Figures 3C, 3D:
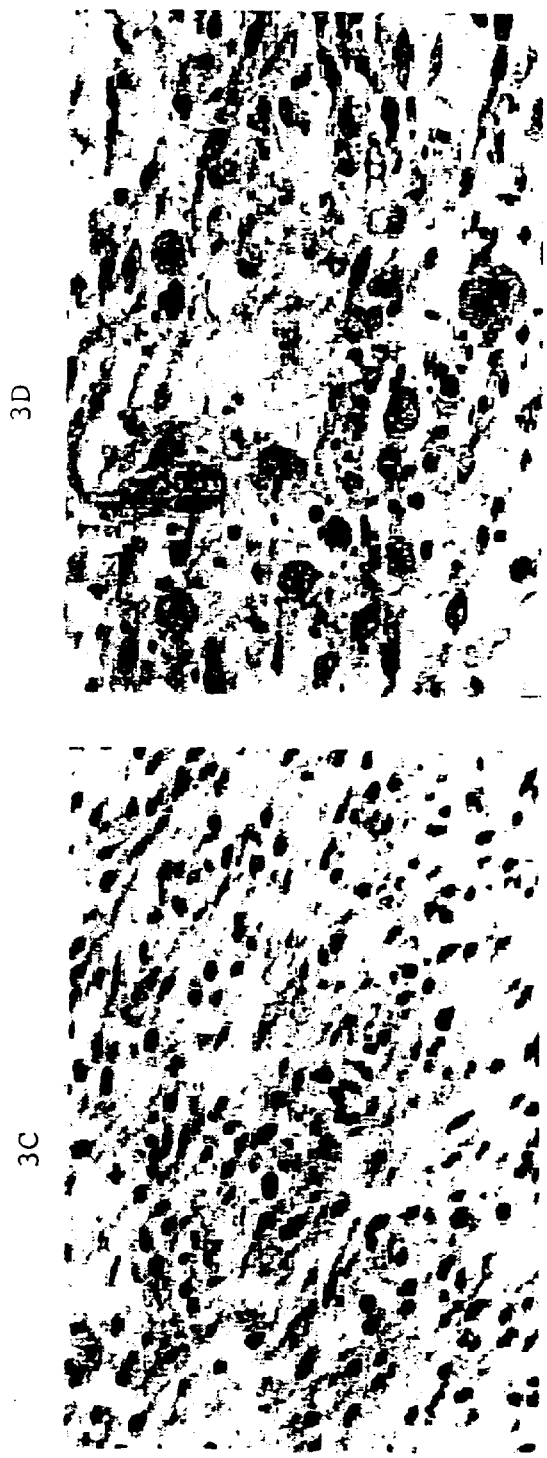
Figure 3E:
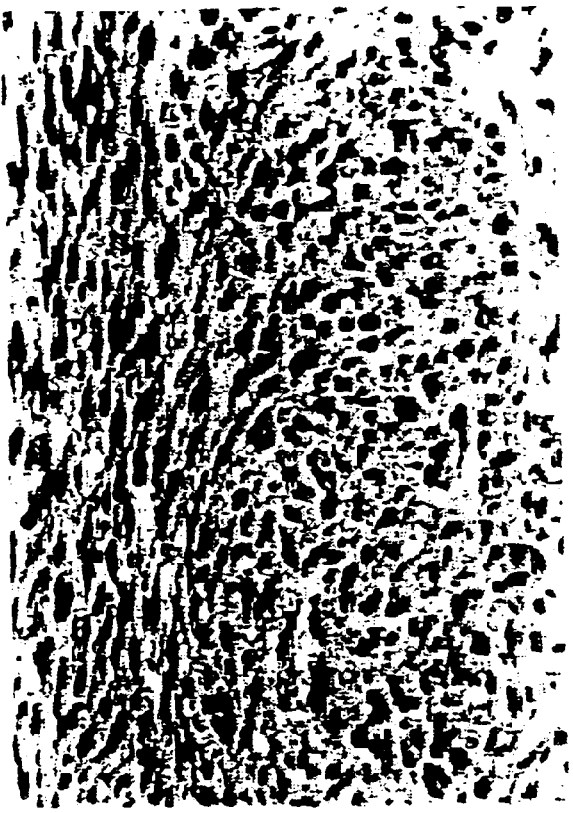
Figure 3F:
Figures 3G, 3H:
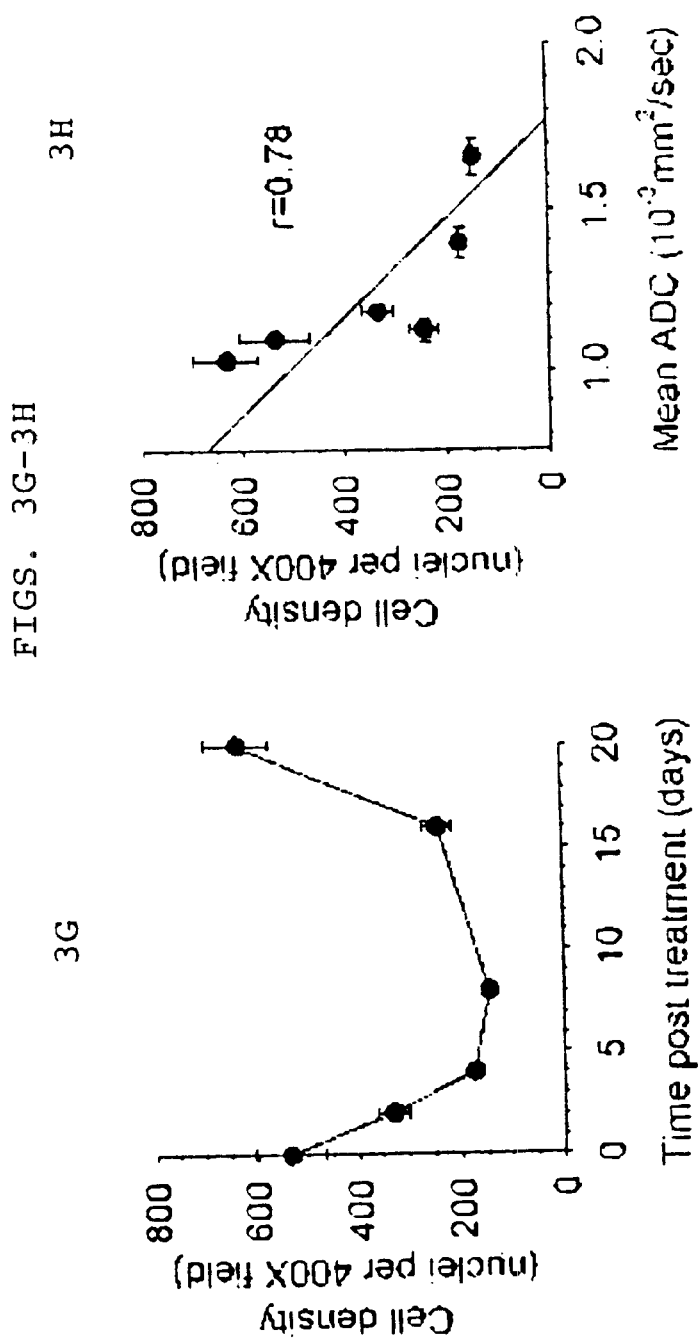
FIG. 3G shows the time course of cell density changes following anti-cancer treatment.
FIG. 3H shows the mean tumor ADC values measured at each time point, as described in detail in Example 1, below.

Histological sections of the 9L tumors at selected intervals following $2\times LD_{10}$ BCNU treatment are presented in FIGS. 3A to 3F. FIG. 3A shows images of H & E stained sections of intra-cerebral 9L tumors treated with a single $2\times LD_{10}$ dose of BCNU. The images were obtained on the day of treatment (FIG. 3A, upper panel, left) and on post-treatment at days 2 (FIG. 3B, upper panel, right), 4 (FIG. 3C, middle panel, left), 8 (FIG. 3D, middle panel, right), 16 (FIG. 3E, lower panel, left) and 20 (FIG. 3F, lower panel, right). FIG. 3G shows cell density measurements from histological 9L tumor sections over time before and following treatment with a 2×LD$_{10}$ dose of BCNU. FIG. 3H shows a plot of 9L tumor cell density versus mean ADC with linear regression fit demonstrating a significant correlation (Y=1.5−0.0009X; r=0.78; P=0.041). The H & E stained sections illustrate the temporal evolution of the histopathological changes of the tumor after treatment.

As is seen in the H & E stained sections, following BCNU treatment, a progressive increase in tumor extracellular space is observed reaching a maximum at about 8 days post-treatment. There was also an increase in pleomorphism, giant cells, and cells with the characteristic morphological features of apoptosis. A lymphocyte-predominant, mixed inflammatory response was evident 6 days after BCNU administration. At 16 days after BCNU therapy, the extracellular space began to diminish and regions of dense regrowth of tumor cells became more predominant. The histology of recurrent tumor is indistinguishable from that of untreated tumor. Tumor cellularity, defined as the number of nuclei in a 400× filed was measured on digitized sections. FIG. 3G (lower left) shows the time course of cell density changes following BCNU treatment. The measured mean tumor cellularity at each time point after BCNU treatment correlated well (r=0.78, P=0.041) with the mean tumor ADC values measured at that respective time point, as shown in FIG. 3H (lower right).

Clinical Studies

Figures 4A, 4B:
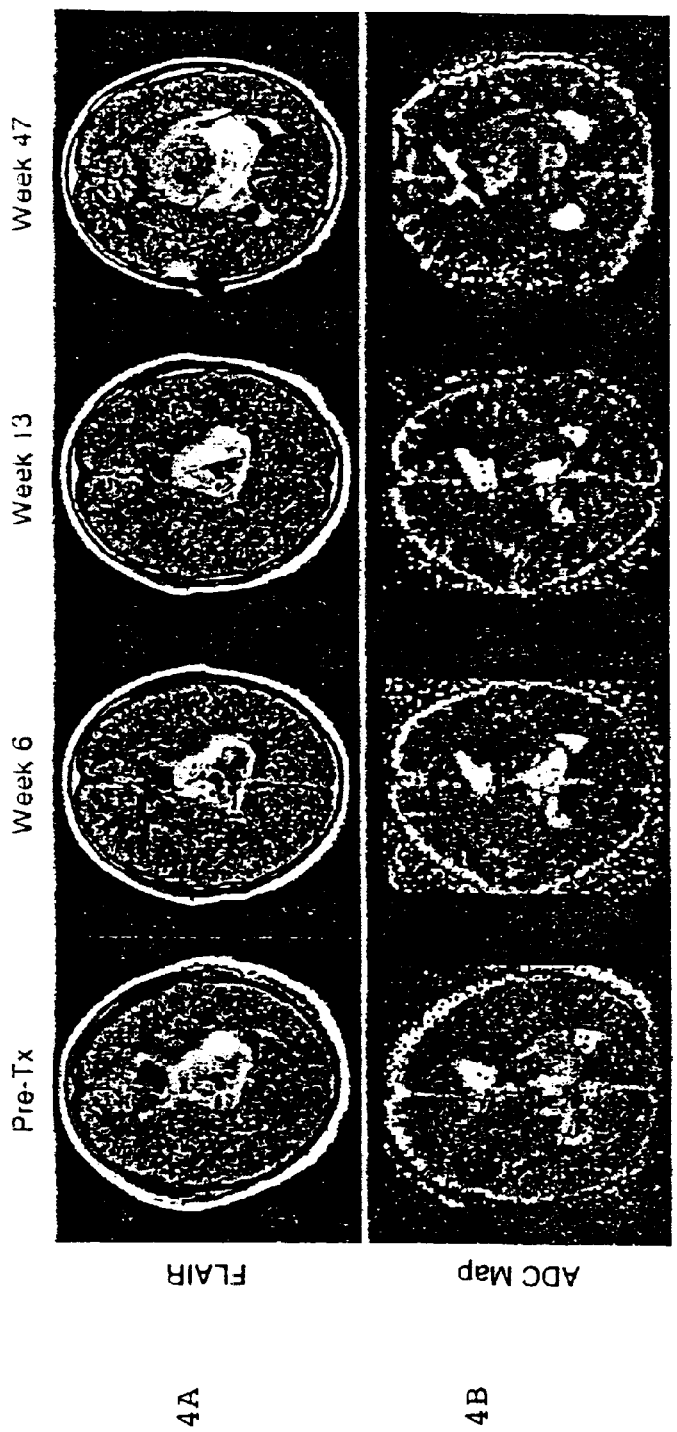
FIG. 4A shows the progress of therapy of a patient with a large thalamic primitive neuroectodermal tumor—representative FLAIR-weighted MR images of a human brain obtained prior to treatment and 6, 13, and 47 weeks after a radiation dose to the tumor field.
FIG. 4B shows corresponding quantitative ADC maps at the same time intervals after radiation treatment; the lower panel shows tumor ADC histograms (FIG. 4C); difference histograms (FIG. 4D) and the mean ADC changes over time (FIG. 4E), as described in detail in Example 1, below.
Figures 4C, 4D, 4E:
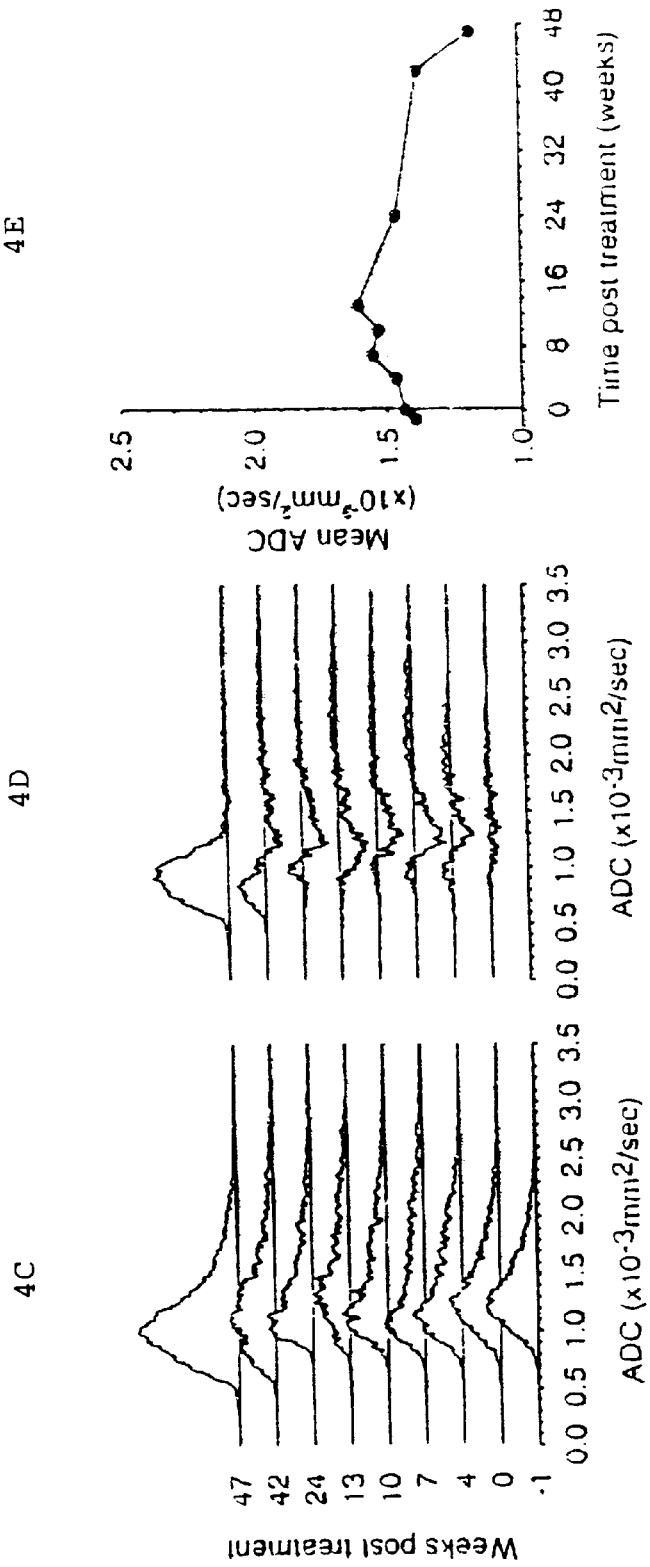

The progress of therapy of a patient with a large thalamic primitive neuroectodermal tumor (PNET) was followed using the methods of the invention. The patient displayed a weak therapeutic response to radiation therapy with carboplatin radiosensitization. FIG. 4A shows representative FLAIR-weighted MR images obtained prior to treatment and 6, 13, and 47 weeks after a 55.8 Gy dose to the tumor field, and 3600 cGy dose to the craniospinal axis with corresponding quantitative ADC maps at the same time intervals (FIG. 4B). At 24 weeks post treatment, the tumor volume had shrunk by 19%, and the patient was classified as having "stable disease" according to standard criteria, as described by, e.g., Macdonald (1990) J. Clin. Oncol. 8:1277–1280. Rapid regrowth of the tumor is evident by week 47. The lower panel shows tumor ADC histograms (FIG. 4C), difference histograms (FIG. 4D) and the mean ADC changes over time (FIG. 4E). The tumor did not enhance with gadolinium contrast on T1-weighted images. Tumor growth resumed by post-therapy week 47. ADC maps obtained from this patient using the methods of the invention demonstrate an area of increased water diffusion in the posterior portion of the mass. Diffusion changes were not observed in the left, anterior portion of the mass (right on images). Shown in FIG. 4C is a stack plot of diffusion histograms of all tumor pixels, along with difference histograms obtained by subtracting pre-treatment from post-treatment histograms, seen in FIG. 4D. For this patient, there was subtle evidence of an early weak positive therapeutic response early on 4 weeks into treatment identified by an increase in pixel area greater than 1.5 ADC units (shaded area). The mean ADC plot (FIG. 4E) indicates a 10% increase in ADC 12 weeks from the start of therapy. During tumor regrowth, a dramatic decline in mean ADC value was observed. The difference plots accentuate the relative shift between water environments, e.g. an increase in quantity of high diffusion pixels (shaded area) with proportional loss in low diffusion pixels (unshaded area) suggest a positive therapeutic change.

Figure 5A:
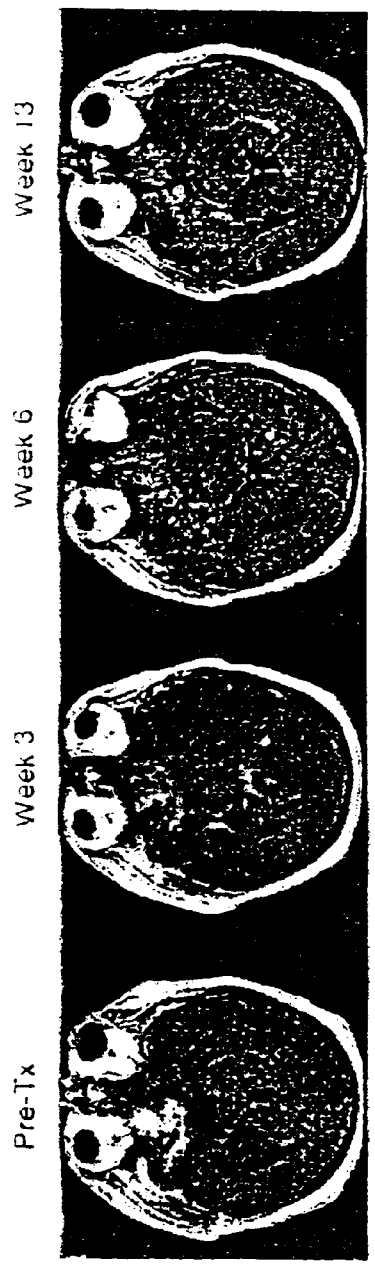
FIG. 5A shows an example of a patient with an oligodendroglioma who responded to PCV chemotherapy—gadolinium-enhanced T1 images (at time 0 (pre-treatment), and 3, 6, and 13 week of treatment) of a 41 year old male with a deep midline, bilateral oligodendroglioma treated with procarbazine/CCNU/vincristine (PCV) are shown in FIG. 5A; serial diffusion histograms (FIG. 5B), difference histograms (FIG. 5C), and tumor-mean ADC values (FIG. 5D) demonstrate the magnitude of the water diffusion change, as described in detail in Example 1, below.
Figures 5B, 5C, 5D:
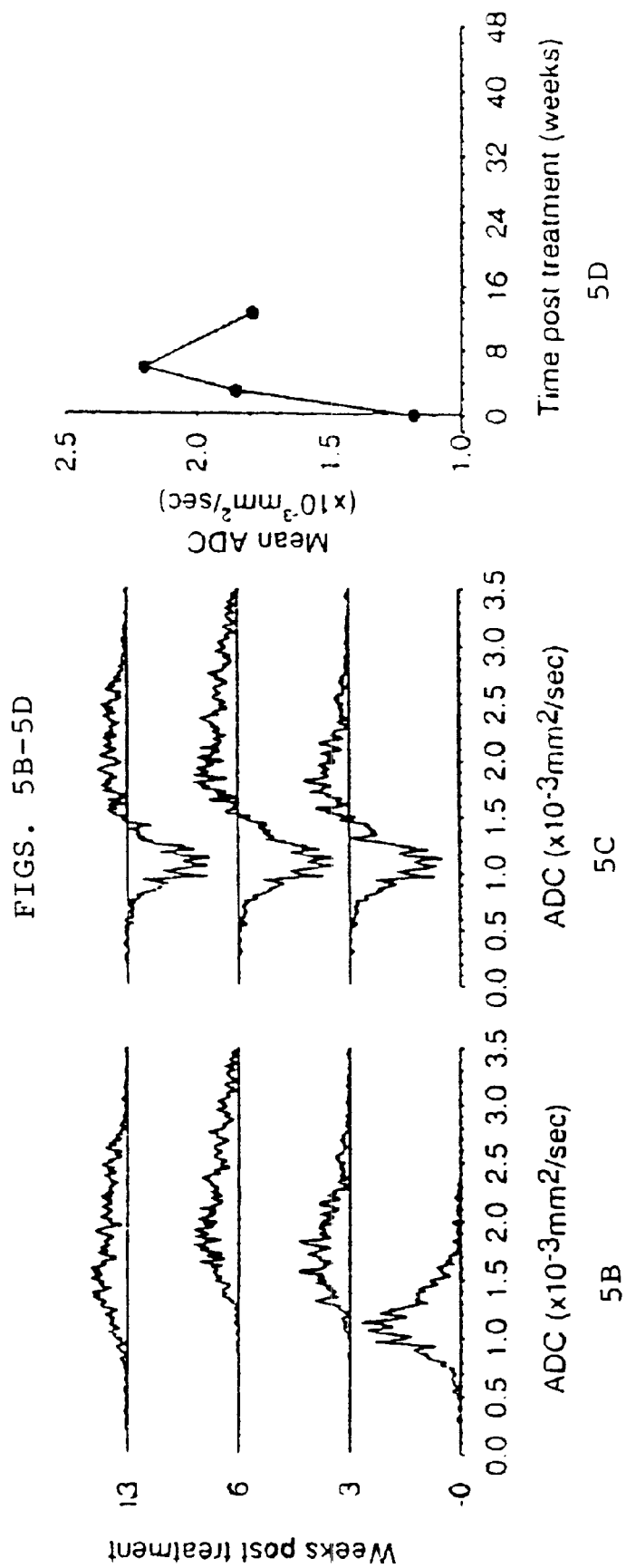

FIG. 5 shows an example of a patient with an oligodendroglioma who responded to PCV chemotherapy. Gadolinium-enhanced T1 images (at time 0 (pre-treatment), and 3, 6, and 13 week of treatment) of a 41 year old male with a deep midline, bilateral oligodendroglioma treated with procarbazine/CCNU/vincristine (PCV) are shown in FIG. 5A. The top panel shows contrast-enhanced T1-weighted MR images. Note the greater rate of tumor water diffusion observed at 3 weeks following start of therapy. Three weeks after the start of PCV therapy, the area of gadolinium contrast-enhancement decreased. The treatment resulted in reduction of the tumor volume by about 25–50%, and the patient was classified as having a "minimal response." The mass effect observed in the FLAIR and T2-weighted MR images (not shown), decreased over the next 10 weeks. Serial diffusion histograms (FIG. 5B), difference histograms (FIG. 5C), and tumor-mean ADC values (FIG. 5D) demonstrate the magnitude of the water diffusion change. A peak diffusion increase of 86% was observed at 6 weeks. The histograms shown in FIG. 5 were derived from regions-of-interest (ROIs) thought to represent residual tumor based on their contrast-enhancing character. Similar results were obtained using larger ROI's defined by hyperintense areas on FLAIR.

Conclusions

These studies demonstrate that the methods of the invention, incorporating diffusion imaging, can generate data and images that can be used to assess treatment responses in individual patients. Thus, the methods of the invention will provide early, reliable prognostic information that will help physicians tailor treatment plans to individual patients and allow alternate therapies to be attempted in a more timely fashion if a tumor appears resistant. The sensitivity of diffusion MRI to changes in tissue structure may also advance experimental therapeutics by providing new tools for analyzing therapeutic outcomes both in laboratory models and clinical trials.

In particular, in these studies, a dose-dependent change in tumor diffusion was observed that appeared to saturate at the 1×LD$_{10}$ dose, corresponding to approximately 1 log kill. The observation of statistically significant changes in tumor ADC values at 4 days after administration of a 0.5×LD$_{10}$ dose, producing a cell kill of 0.2 log, reveals that diffusion is very sensitive to small cell kill values. The apparent saturation at 1 log kill suggests that the dynamic range is greatest at the lower cell kills. This feature could provide for detection of small therapeutic-induced tissue changes required for clinical monitoring of fractionated therapies for brain tumors.

Comparison of tumor histology with MR-measured mean tumor ADC values demonstrated a significant correlation between therapy-induced changes in cellularity and water diffusion. The regression line indicates that "cell-free" tumor, e.g. tumor with zero nuclei per field, would exhibit an ADC of $1.7 \times 10^{-3}$ mm$^2$/sec, which is lower than the ADC of cerebrospinal fluid at body temperature ($3.0 \times 10^{-3}$ mm$^2$/sec). This diffusion restriction is likely due to cell remnants and mucoid substance in the necrotic spaces. Decreases in cellularity reflect an increased volume of water in the extracellular compartment, which could be due to vasogenic edema or shifts of intracellular water to the extracellular space associated with tumor cell necrosis. This study does not provide specific data regarding the relative roles of these processes; however, studies by Ross (1998) Proc. Natl. Acad. Sci. USA 95:7012–7017, demonstrated that BCNU kills approximately 40% of 9L tumor cells at the 0.5×LD$_{10}$ dose. Moreover, vasogenic edema was not observed in contralateral normal brain tissue. These observations are consistent with the hypothesis that water liberated by cell necrosis is a major mechanism for therapy-induced diffusion increase.

The clinical potential of the methods of the invention using diffusion MRI was performed in two patients with different types of primary CNS tumors. The methods detected a modest, early increase in diffusion, followed by a drop in tumor ADC with increased tumor volume during the therapy of the patient with a PNET. This pattern of diffusion changes was consistent with the clinical response of stable disease followed by rapid progressive disease. The data obtained from this patient indicate that diffusion MRI data as collated by the methods of the invention is a very sensitive technique able to detect relatively low levels of tumor cell kill. A stronger diffusion shift would be anticipated in patients more responsive to treatment parallel to the trends observed in the rodent brain tumor studies. A more pronounced diffusion increase was observed in the patient with the oligodendroglioma. This change reflects the ~25–50% reduction in apparent tumor volume.

What is claimed is:

1. A computer program product for use in the detection of changes in rates of water diffusion in a tissue using magnetic resonance imaging (MRI) comprising a computer useable medium comprising a computer readable program code embodied therein, wherein the computer program product is capable of storing and analyzing data input from a MRI device by a process comprising the following steps:
    (a) providing a magnetic resonance imaging (MRI) device capable of outputting data to a computer;
    (b) providing a computer capable of storing and analyzing data input from the MRI device comprising a computer program product embodied therein;
    (c) projecting a sequence of magnetic field gradient pulses and radiofrequency pulses to the tissue of interest by the MRI device and collecting a first set of MRI signals from the tissue and outputting this data to the computer, wherein the MRI device collects MRI signals from the tissue of interest at multiple diffusion sensitivities and diffusion directions;
    (d) analyzing the first set of diffusion-sensitive MRI signal readings by the computer program product to calculate an apparent diffusion coefficient (ADC) value for each diffusion direction, wherein an ADC value corresponds to a spatial origin of the signals used to determine the ADC value, and to generate a first spatial map of ADC values;
    (e) projecting at least a second sequence of magnetic field gradient pulses and radiofrequency pulses and analyzing at least a second set of diffusion-sensitive MRI readings in the same tissue of interest as in steps (c) and (d) to generate at least a second subsequent spatial map of ADC values; and
    (f) compare the first and subsequent spatial maps of ADC values to generate a spatial map that reflects the changes in ADC values over the time the several readings were taken by the MRI, wherein the changes in ADC values reflect the changes in spin diffusion properties which reflect changes in rates of water diffusion in the tissue.

2. A computer system, comprising:
    (a) a processor; and
    (b) a computer program product as set forth in claim 1.

3. A tissue imaging system, comprising:
    (a) a magnetic resonance imaging (MRI) device capable of outputting data to a processor;
    (b) a processor; and
    (c) a computer program product as set forth in claim 1 embodied within the processor.

4. A computer-implemented method for detecting changes in rates of water diffusion in a tissue comprising the following steps:
    (a) providing a magnetic resonance imaging (MRI) device capable of outputting data to a computer;
    (b) providing a computer capable of storing and analyzing data input from the MRI device comprising a computer program product embodied therein;
    (c) projecting a sequence of magnetic field gradient pulses and radiofrequency pulses to the tissue of interest by the MRI device and collecting a first set of MRI signals from the tissue and outputting this data to the computer, wherein the MRI device collects MRI signals from the tissue of interest at multiple diffusion sensitivities and diffusion directions;
    (d) analyzing the first set of diffusion-sensitive MRI signal readings by the computer program product to calculate an apparent diffusion coefficient (ADC) value for each diffusion direction, wherein an ADC value corresponds to a spatial origin of the signals used to determine the ADC value, and to generate a first spatial map of ADC values;
    (e) projecting at least a second sequence of magnetic field gradient pulses and radiofrequency pulses and analyzing at least a second set of diffusion-sensitive MRI readings in the same tissue of interest as in steps (c) and (d) to generate at least a second subsequent spatial map of ADC values; and
    (f) compare the first and subsequent spatial maps of ADC values to generate a spatial map that reflects the changes in ADC values over the time the several readings were taken by the MRI, wherein the changes in ADC values reflect the changes in spin diffusion properties which reflect changes in rates of water diffusion in the tissue.

5. The computer-implemented method of claim 4, wherein the computer program product uses the spatial map that reflects the changes in ADC values over the time the several readings were taken by the MRI to generate a histogram.

6. The computer-implemented method of claim 4, wherein the tissue is brain or spinal cord tissue.

7. The computer-implemented method of claim 4, wherein the tissue is internal organ, skeletal or muscle tissue.

8. The computer-implemented method of claim 4, wherein the tissue is a diseased tissue.

9. The computer-implemented method of claim 8, wherein the diseased tissue is a cancer.

10. The computer-implemented method of claim 4, wherein the diseased tissue is an injured or inflamed tissue.

11. The computer-implemented method of claim 4, wherein the tissue has been exposed to a drug, a biological agent, hyperthermia, hypothermia, a radiation or a combination thereof.

12. The computer-implemented method of claim 11, wherein the tissue has been exposed to an antivascular therapy.

13. The computer-implemented method of claim 11, wherein radiation is a radiotherapy or a photodynamic therapy or a combination thereof.

14. The computer-implemented method of claim 4, wherein an increase in the rate of water diffusion as shown by the spatial map that reflects the changes in ADC values over the time indicates cell damage or tissue microvasculature damage.

15. The computer-implemented method of claim 4, wherein a rate of water diffusion higher or lower than considered normal for the tissue of interest indicates cell damage or tissue microvasculature damage.

16. The computer-implemented method of claim 4, wherein the method is applied to determine the effectiveness of an organ or a tissue transplant.

17. The computer-implemented method of claim 4, wherein the method is applied to determine the effectiveness of a therapy for a condition or a disease or an injury.

18. The computer-implemented method of claim 17, wherein the therapy is for a cancer and an increase in diffusion indicates tumor cell damage or tumor microvasculature damage, thereby indicating the effectiveness of the cancer therapy.

19. The computer-implemented method of claim 17, wherein the therapy is for an injured or inflamed tissue and a charge in diffusion indicates tissue repair or decreased inflammation, thereby indicating the effectiveness of the therapy.

20. The computer-implemented method of claim 4, wherein a change in diffusion indicates tissue repair.

21. The computer-implemented method of claim 4, wherein ADC values from a defined spatial subsection of the tissue taken over time is used to generate a statistical data reduction of data in that spatial subsection.

22. The computer-implemented method of claim 21, wherein the statistical data reduction comprises a mean standard deviation, a pixel count or a volume of tissue or a combination thereof.

23. The computer-implemented method of claim 21, wherein a histogram is generated from the statistical data reduction.

24. The computer-implemented method of claim 23, wherein a histogram reflecting changes in statistical data reduction sets over time is generated.

25. The computer-implemented method of claim 4, wherein the first set of diffusion-sensitive MRI signal readings is generated before initiation of a therapy.

26. The computer-implemented method of claim 25, wherein a subsequent set of diffusion-sensitive MRI signal readings is generated after initiation of a therapy.

27. The computer-implemented method of claim 26, wherein a subsequent set of diffusion-sensitive MRI signal readings is generated at a time appropriate for a therapeutic change in tissue.

* * * * *